(12) United States Patent
Sisko et al.

(10) Patent No.: US 6,335,448 B1
(45) Date of Patent: Jan. 1, 2002

(54) METHOD FOR THE SYNTHESIS OF QUINOLINE DERIVATIVES

(75) Inventors: Joseph Sisko, Hatfield; Mark Mellinger, Telford; Conrad Kowalski, Paoli, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/508,358

(22) PCT Filed: Sep. 17, 1998

(86) PCT No.: PCT/US98/19434
§ 371 Date: Mar. 9, 2000
§ 102(e) Date: Mar. 9, 2000

(87) PCT Pub. No.: WO99/14196
PCT Pub. Date: Mar. 25, 1999

Related U.S. Application Data

(60) Provisional application No. 60/059,303, filed on Sep. 17, 1997.

(51) Int. Cl.$^7$ .................... C07D 215/38; C07D 215/20; C07D 215/36
(52) U.S. Cl. ........................................ 546/169; 546/170
(58) Field of Search .................................. 546/169, 170

(56) References Cited

U.S. PATENT DOCUMENTS 5,811,553 A * 9/1998 Farina

FOREIGN PATENT DOCUMENTS

WO 95/32948 * 12/1995

OTHER PUBLICATIONS

Casreact 130:196653, abstract of Donovan, US Patent 5,874,587, 1999, filed 1996.*

Casreact 128:243932, abstract of Lasikova, Chem. Pap. 51(6b), 408–411, 1997.*

Casreact 110:135063, abstract of Atwell, J. Med. Chem 32(2) 396–401, 1989.*

Chem. abstr., vol. 125, No. 17, Oct. 17, 1996, p. 1084, col. 1, the abstract No. 221603, Fujwara, J. et al. "Preparation of N–4(–quinolylcarbonyl) guanidines as hydrogen ion–sodium antiporter inhibitor".

Chem. abstr., vol. 110, No. 15, Apr. 10, 1989, p. 697, col. 1, the abstract No. 135063, Atwell, G.J. et al. Potential antitumor agents 57. 2–phenylquinolines–8–carboxamides as minimal DNA–intercalating antitumor agents with in vivo solid tumor activity.

* cited by examiner

*Primary Examiner*—D. Margaret Seaman
(74) *Attorney, Agent, or Firm*—Nora Stein-Fernandez; Stephen Venetianer; Charles M. Kinzig

(57) ABSTRACT

This invention relates to novel intermediates and processes for preparing pharmaceutically active quinoline compounds, including (−)-(S)-N-(α-ethylbenzyl)-3-hydroxy-2-phenylquinoline-4-carboxamide.

17 Claims, No Drawings

METHOD FOR THE SYNTHESIS OF QUINOLINE DERIVATIVES

This is a 371 of International Application PCT/US98/19434 filed Sep. 17, 1998, which claims benefit from the following Provisional Application No. 60/059/303 filed Sep. 17, 1997.

FIELD OF THE INVENTION

This invention relates to novel intermediates and processes for preparing pharmaceutically active quinoline compounds, including (−)-(S)-N-(α-ethylbenzyl)-3-hydroxy-2-phenylquinoline-4-carboxamide.

BACKGROUND OF THE INVENTION

Compounds of the structural formula (I)

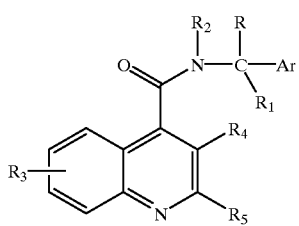

Formula (I)

or a pharmaceutically acceptable salt form thereof, wherein:

Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, an optionally substituted phenyl group or a phenyl $C_{1-6}$ alkyl group, an optionally substituted five-membered heteroaromatic ring comprising up to four heteroatom selected from O and N, hydroxy $C_{1-6}$ alkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxycarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl; or is a group —$(CH_2)_p$— when cyclized onto Ar, where p is 2 or 3;

$R_1$ and $R_2$, which may be the same or different, are independently hydrogen or $C_{1-6}$ linear or branched alkyl, or together form a —$(CH_2)_n$— group in which n represents 3, 4, or 5; or $R_1$ together with R forms a group —$(CH_2)_q$—, in which q is 2, 3,4 or 5;

$R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —$O(CH_2)_r$—$NT_2$, in which r is 2, 3, or 4 and T is $C_{1-6}$ alkyl or it forms a heterocyclic group

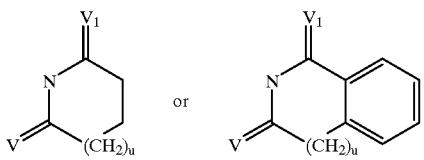

in which V and $V_1$ are hydrogen and u is 0, 1 or 2;

—$O(CH_2)_s$—$OW_2$ in which s is 2, 3, or 4 and W is $C_{1-6}$ alkyl; hydroxyalkyl, mono-or di-alkylaminoalkyl, acylamino, alkylsulphonylamino, aminoacylamino, mono- or di-alkylaminoacylamino; with up to four $R_3$ substituents being present in the quinoline nucleus;

or $R_4$ is a group —$(CH_2)_t$— when cyclized onto $R_5$ as aryl, in which t is 1, 2, or 3; and $R_5$ is branched or linear $C_{1-6}$ alkyl, $C_{3-7}$ cycloalkyl, $C_{4-7}$ cycloalkylalkyl, optionally substituted aryl, wherein the optional substituent is one of hydroxy, halogen, $C_{1-6}$ alkoxy or $C_{1-6}$ alkyl, or an optionally substituted single or fused ring heterocyclic group, having aromatic character, containing from 5 to 12 ring atoms and comprising up to four hetero-atoms in the or each ring selected from S, O, N; are NK-3 antagonists and are useful in treating pulmonary disorders (asthma, chronic obstructive pulmonary diseases (COPD), airway hyperreactivity, cough), skin disorders and itch (for example, atopic dermatitis and cutaneous wheal and flare), neurogenic inflammation, CNS disorders (Parkinson's disease, movement disorders, anxiety), convulsive disorders (for example epilepsy), renal disorders, urinary incontinence, ocular inflammation, inflammatory pain, eating disorders (food intake inhibition), allergic rhinitis, neurodegenerative disorders (for example Alzheimer's disease), psoriasis, Huntington's disease, and depression. A particularly useful NK-3 receptor antagonist falling within the genus of formula (I) is (−)-(S)-N-(α-ethylbenzyl)-3-hydroxy-2-phenylquinoline-4-carboxamide. Such compounds, and methods for preparing the compounds, are disclosed in PCT/EP95/02000, published Dec. 7, 1995, as WO 95/32948, the disclosures of which are incorporated herein by reference.

NK-3 receptor antagonists are useful in treating the symptoms of COPD and urinary incontinence in mammals. An example of such a compound is the potent antagonist (−)-(S)-N-(α-ethylbenzyl)-3-hydroxy-2-phenylquinoline-4-carboxamide. While the route published in PCT/EP95/02000, published Dec. 7, 1995, as WO 95/32948, requires only three steps, the synthesis is plagued with costly starting materials (e.g., 2-Scheme 1, α-methoxyacetophenone) and chromatography in the low-yielding final step. As is illustrated in Scheme 1, the DCC-mediated (dicyclohexyl carbodiimide) coupling of 4-Scheme 1, 3-hydroxy-2-phenylquinoline-4-carboxylic acid, with (S)-1-phenyl propylamine led to a 30–50% isolated yield of (−)-(S)-N-(α-ethylbenzyl)-3-hydroxy-2-phenylquinoline-4-carboxamide along with 10–20% of compound 6-Scheme 1, (S)-2-Phenyl-4-[[(1-phenylpropyl)-amino]carbonyl]-3-quinolinyl-3-hydroxy-2-phenyl-4-quinolinecarboxylate, requiring chromatography for its removal. Without being bound to any particular theory, (S)-2-Phenyl-4-[[(1-phenylpropyl)amino]carbonyl]-3-quinolinyl-3-hydroxy-2-phenyl-4-quinoline-carboxylate appears to form as a by-product of an attack of the phenolic oxygen of (−)-(S)-N-(α-ethylbenzyl)-3-hydroxy-2-phenylquinoline-4-carboxamide to the DCC-activated acid of 3-hydroxy-2-phenylquinoline-4-carboxylic acid.

Scheme 1

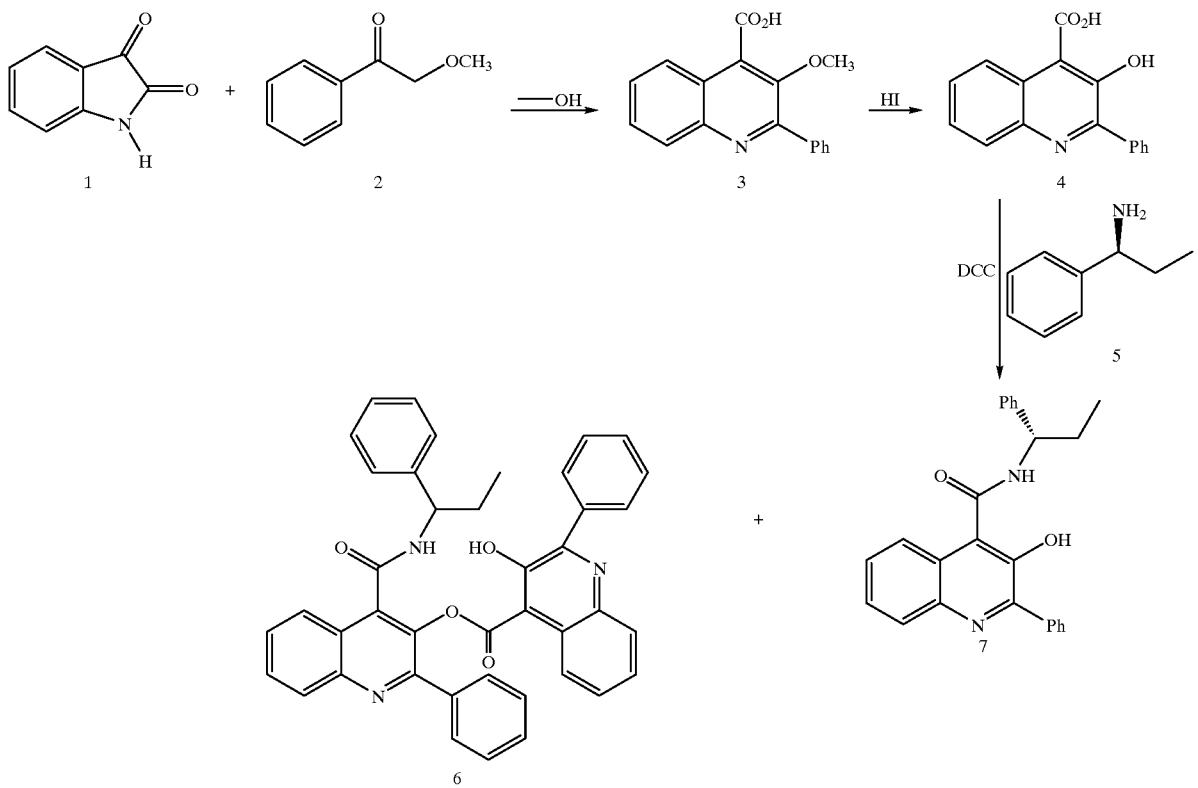

Given the known synthesis for quinoline NK-3 receptor antagonists of formula (I), there was a need for an environmentally favorable, commercially feasible, cheaper and more efficient process, with increased yields, for coupling an ortho-hydroxy acid with an amine to provide (−)-(S)-N-(α-ethylbenzyl)-3-hydroxy-2-phenylquinoline-4-carboxamide and related compounds. The present invention provides new synthetic processes for the synthesis of (−)-(S)-N-(α-ethylbenzyl)-3-hydroxy-2-phenylquinoline-4-carboxamide and related compounds, which eliminates the need for the use of (2-Scheme 1, α-methoxyacetophenone), the need for the use of a chromatography step to remove 6-Scheme 1, (S)-2-Phenyl-4-[[(1-phenylpropyl)-amino]carbonyl]-3-quinolinyl-3-hydroxy-2-phenyl-4-quinolinecarboxylate, and which increases the yield of desired product from between 30 and 50% to greater than 70%. In addition, according to this invention, the hydrochloride salt of the free base of (−)-(S)-N-(α-ethylbenzyl)-3-hydroxy-2-phenylquinoline-4-carboxamide and related compounds is optionally prepared, in one reaction vessel, without the need to isolate and purify the free base.

Cragoe et al., *J. Org. Chem.*, 1953, 19, pp. 561–569, discloses the reaction of 7-carboxy-substituted isatins with substituted phenacyl acetates to provide derivatives of 3-hydroxycinchoninic acid. Phenacyl acetates are known and/or can be prepared according to Normant et al., *Synthesis*, 1975, pp. 805–807, which discloses reacting potassium acetate with alkyl bromides catalyzed by diamines in acetonitrile to provide such acetates. An optimized method for preparing anhydro-O-carboxysalicylic acid and anhydro-O-carboxyglycolic acid is disclosed in Davies, W. H., *J. Chem. Soc.*, 1951, pp. 1357–1359. A preparation for five-membered ring sulfites from the reaction of thionyl chloride and α-hydroxycarboxylic acids is discussed in Blackbourn et al., *J. Chem. Soc.* (C), 1971, pp. 257–259.

None of the above-cited documents describe the methods of the present invention for the synthesis of quinoline NK-3 receptor antagonists of formula (I) or formula (Ia) or the compounds of the invention which are useful as intermediates for the synthesis of such quinoline NK-3 receptor antagonists.

SUMMARY OF THE INVENTION

The objects of this invention are to provide novel intermediates and processes for preparing these intermediates which are useful in the preparation of pharmaceutically active compounds.

Accordingly, in one aspect, this invention is in a method for preparing a compound of formula (I):

Formula (I)

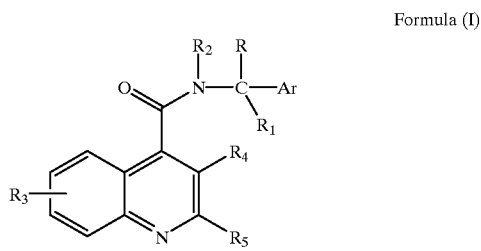

or a pharmaceutically acceptable salt form thereof, wherein:
Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, an optionally substituted phenyl group or a phenyl $C_{1-6}$ alkyl group, an optionally substituted five-membered heteroaromatic ring comprising up to four heteroatom selected from O and N, hydroxy $C_{1-6}$ alkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxycarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl; or is a group $—(CH_2)_p—$ when cyclized onto Ar, where p is 2 or 3;

$R_1$ and $R_2$, which may be the same or different, are independently hydrogen or $C_{1-6}$ linear or branched alkyl, or together form a $—(CH_2)_n—$ group in which n represents 3, 4, or 5; or $R_1$ together with R forms a group $—(CH_2)_q—$, in which q is 2, 3,4 or 5;

$R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, $—O(CH_2)_r—NT_2$, in which r is 2, 3, or 4 and T is $C_{1-6}$ alkyl or it forms a heterocyclic group

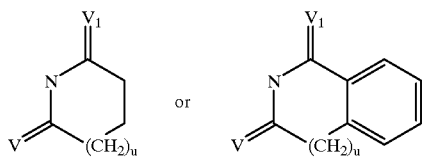

in which V and $V_1$ are hydrogen and u is 0, 1 or 2;

$—O(CH_2)_s—OW_2$ in which s is 2, 3, or 4 and W is $C_{1-6}$ alkyl; hydroxyalkyl, mono-or di-alkylaminoalkyl, acylamino, alkylsulphonylamino, aminoacylamino, mono- or di-alkylaminoacylamino; with up to four $R_3$ substituents being present in the quinoline nucleus;

or $R_4$ is a group $—(CH_2)_t—$ when cyclized onto $R_5$ as aryl, in which t is 1, 2, or 3; and $R_5$ is branched or linear $C_{1-6}$ alkyl, $C_{3-7}$ cycloalkyl, $C_{4-7}$ cycloalkylalkyl, optionally substituted aryl, wherein the optional substituent is one of hydroxy, halogen, $C_{1-6}$ alkoxy or $C_{1-6}$ alkyl, or an optionally substituted single or fused ring heterocyclic group, having aromatic character, containing from 5 to 12 ring atoms and comprising up to four heteroatoms in the or each ring selected from S, O, N; comprising;

1) adding a compound of formula (III):

Formula (III)

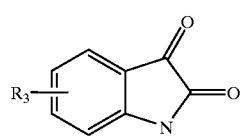

to base in a suitable solvent, to form a first reaction mixture, adding to the first reaction mixture a compound of formula (II):

Formula (II)

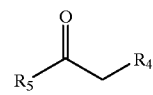

to form a second reaction mixture, and heating the second reaction mixture to form a compound of formula (IV):

Formula (IV)

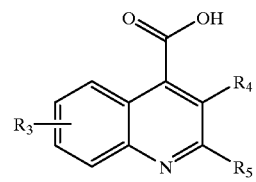

2) isolating the compound of formula (IV) and then reacting the compound of formula (IV), in a suitable solvent, with a base to form a third reaction mixture, cooling the third reaction mixture, and adding a carbonyl-activating agent to form a fourth reaction mixture;

3) adding a compound of formula (V):

Formula (V)

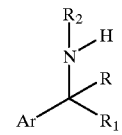

to the fourth reaction mixture to form a fifth reaction mixture;

4) heating the fifth reaction mixture; and 5) optionally converting the compound of formula (I) to a pharmaceutically acceptable salt, wherein Ar, R, $R_1$, $R_2$, $R_3$, $R_4$, and $R_5$ as used in a compound of formulae (II) through (VI) are as defined for a compound of formula (I).

In another aspect, this invention is in a method for preparing (−)-(S)-N-(α-ethylbenzyl)-3-hydroxy-2-phenylquinoline-4-carboxamide comprising:

1) adding isatin to base in a suitable solvent, to form a first reaction mixture, adding to the first reaction mixture an α-acetoxy ketone to form a second reaction mixture, and heating the second reaction mixture to form an α-hydroxy acid;

2) isolating the α-hydroxy acid and then reacting it, in a suitable solvent, with a base to form a third reaction mixture, cooling the third reaction mixture, and adding a carbonyl-activating agent to form a fourth reaction mixture;

3) adding a primary or secondary amine, e.g., (S)-1-phenyl propylamine, to the fourth reaction mixture to form a fifth reaction mixture; and 4) heating the fifth reaction mixture.

In yet another aspect, this invention is in a method for preparing (−)-(S)-N-(α-ethylbenzyl)-3-hydroxy-2-phenylquinoline-4-carboxamide comprising:

1) reacting an α-hydroxy acid, in a suitable solvent, with a base to form a first reaction mixture, cooling the first reaction mixture, and adding a carbonyl-activating agent to form a second reaction mixture;

2) adding a primary or secondary amine to the second reaction mixture to form a third reaction mixture;

3) heating the third reaction mixture; and 4) optionally converting (−)-(S)-N-(α-ethylbenzyl)-3-hydroxy-2-phenylquinoline-4-carboxamide to a pharmaceutically acceptable salt.

In still another aspect, this invention is in a novel intermediate compound of formula (VII):

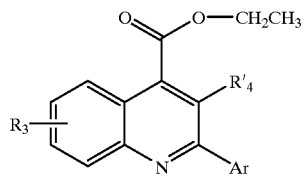

Formula (VII)

wherein Ar and $R_3$ are as defined above for formula (I), and wherein $R'_4$ is OH or —O—C(O)—$R_a$, wherein $R_a$ is $C_{1-6}$ alkyl, aryl, preferably methyl.

In a further aspect, this invention is in a novel intermediate compound of formula (VIII):

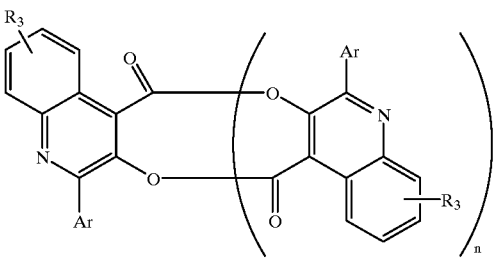

Formula (VIII)

wherein:

Ar and $R_3$ are as defined for a compound of formula (I) as claimed in claim 1; and n is 1 or 3.

DETAILED DESCRIPTION OF THE INVENTION

In developing the instant inventive methods, particularly when for the compound of formula (IV), $R_4$ is hydroxy, it was desirable to activate the carboxyl group of the 4-acid moiety towards addition, while at the same time, and in a single operation, to protect the phenol oxygen of $R_4$. According to known procedures (see, e.g., Davies, W. H., *J. Chem. Soc.*, 1951, pp. 1357–1359) coupling of an amine with an activated α-hydroxy acid provides a compound wherein the addition of the amine occurs at an undesirable position, thereby teaching away from producing the desired α-hydroxy amide. In addition, this procedure requires using phosgene ($COCl_2$) as a reagent, a very toxic compound, requiring specialized equipment for industrial application.

Further, it is known that using thionyl chloride, one can couple acids with amines to provide amides. However, using that method to provide amides from an (α-hydroxy acid starting material, one of skill in the art would expect a result of lower yields and undesired side products, (see Gnaim, J. M. et al., *J. Org. Chem.*, 1991, 56, p. 4525) particularly due to the (α-hydroxy moiety.

Without being bound to any particular mechanistic theory for the instant inventive process, it is believed that in contrast to disclosures in the art, the coupling step between the compound of formula (IV) and an amine of formula (V) appears to proceed through, inter alia, novel intermediates of formula (VII) and formula (VIII), both of which are converted to desired product, thus increasing the yield two-fold. Using the instant method therefore, avoids the formation of undesired side-products which must be removed by some form of purification, e.g., chromatography. Indeed, while these novel intermediates, as well as the compound of formula (VI), are still produced in situ by the methods of this invention, they are all easily converted to desired product, thus accounting for a more efficient process (greater than 70% yields are achieved with this process), as well as avoiding the need for a chromatography step.

Thus, the present invention provides a process for preparing a compound of formula (I):

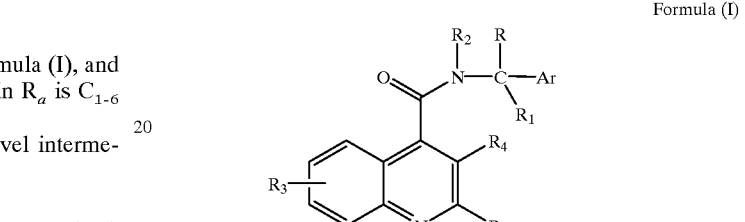

Formula (I)

or a pharmaceutically acceptable salt form thereof, wherein:

Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, an optionally substituted phenyl group or a phenyl $C_{1-6}$ alkyl group, an optionally substituted five-membered heteroaromatic ring comprising up to four heteroatom selected from O and N, hydroxy $C_{1-6}$ alkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxycarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl; or is a group —$(CH_2)_p$— when cyclized onto Ar, where p is 2 or 3;

$R_1$ and $R_2$, which may be the same or different, are independently hydrogen or $C_{1-6}$ linear or branched alkyl, or together form a —$(CH_2)_n$— group in which n represents 3, 4, or 5; or $R_1$ together with R forms a group —$(CH_2)_q$—, in which q is 2, 3,4 or 5;

$R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —$O(CH_2)_r$—$NT_2$, in which r is 2, 3, or 4 and T is $C_{1-6}$ alkyl or it forms a heterocyclic group in which V and $V_1$ are hydrogen and u is 0, 1 or 2;

—$O(CH_2)_s$—$OW_2$ in which s is 2, 3, or 4 and W is $C_{1-6}$ alkyl; hydroxyalkyl, mono-or di-alkylaminoalkyl, acylamino, alkylsulphonylamino, aminoacylamino, mono-or di-alkylaminoacylamino; with up to four $R_3$ substituents being present in the quinoline nucleus;

or $R_4$ is a group —$(CH_2)_t$— when cyclized onto $R_5$ as aryl, in which t is 1, 2, or 3; and $R_5$ is branched or linear $C_{1-6}$ alkyl, $C_{3-7}$ cycloalkyl, $C_{4-7}$ cycloalkylalkyl, optionally substituted aryl, wherein the optional substituent is one of hydroxy, halogen, $C_{1-6}$ alkoxy or $C_{1-6}$ alkyl, or an optionally substituted single or fused ring heterocyclic group, having aromatic character, containing from 5 to 12 ring atoms and comprising up to four heteroatoms in the or each ring selected from S, O, N; comprising:

1) adding a compound of formula (III):

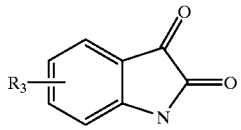

Formula (III)

to aqueous base in a suitable solvent, to form a first reaction mixture, adding to the first reaction mixture a compound of formula (II):

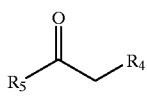

Formula (II)

to form a second reaction mixture, and heating the second reaction mixture to form a compound of formula (IV):

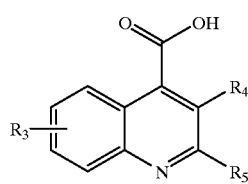

Formula (IV)

2) isolating the compound of formula (IV) and then reacting the compound of formula (IV), in a suitable solvent, with a base to form a third reaction mixture, cooling the third reaction mixture, and adding a carbonyl activating agent to form a fourth reaction mixture;

3) adding a compound of formula (V):

Formula (V)

$$\underset{Ar}{\overset{R_2}{\underset{R_1}{\overset{|}{N}}}}\overset{H}{\underset{R}{}}$$

to the fourth reaction mixture to form a fifth reaction mixture;

4) heating the fifth reaction mixture; and 5) optionally converting the compound of formula (I) to a pharmaceutically acceptable salt, wherein Ar, R, $R_1$, $R_2$, $R_3$, $R_4$, and $R_5$ as used in a compound of formulae (II) through (VI) are as defined for a compound of formula (I).

It will be understood that when $R_4$ in the compound of formula (IV) is defined as hydroxy, then $R_4$ in the compound of formula (II) should be a protected alcohol, e.g., protected by an acetate group, which is eventually deprotected.

It will also be understood that the fifth reaction mixture comprises the compound of formula (I) and a compound of formula (VI):

Formula (VI)

Upon heating the fifth reaction mixture, the compound of formula (VI) is converted to desired product of formula (I).

An example of Ar as phenyl, is a phenyl optionally substituted by hydroxy, halogen, $C_{1-6}$ alkoxy or $C_{1-6}$ alkyl. When Ar is substituted, preferably, the substituents are independently one or more of halogen or $C_{1-6}$ alkyl.

Examples of Ar as a heterocyclic group are thienyl, pyridyl, and the like.

Examples of Ar as a $C_{5-7}$ cycloalkdienyl group is cyclohexadienyl.

A preferred group of compounds is when Ar is phenyl, optionally substituted by $C_{1-6}$ alkyl or halogen; thienyl, furyl, pyrryl, thiazolyl, or a $C_{5-7}$ cycloalkdienyl group. A further preferred group is when Ar is phenyl, optionally substituted by $C_{1-6}$ alkyl or halogen; thienyl or a $C_{5-7}$ cycloalkdienyl group. A particularly preferred group of compounds is when Ar is phenyl, 2-chlorophenyl, 2-thienyl or cyclohexadienyl. Ar is most preferably phenyl.

Examples of R are as follows:
$C_{1-8}$ alkyl: methyl, ethyl, n-propyl, iso-propyl, n-butyl, heptyl, and the like;
phenyl $C_{1-6}$ alkyl: benzyl, and the like;
hydroxy $C_{1-6}$ alkyl: —$CH_2OH$, —$CH_2CH_2OH$, —CH(Me)OH;
di $C_{1-6}$ alkylaminoalkyl: —$CH_2NMe_2$;
$C_{1-6}$ alkoxylalkyl: $CH_2OMe$;
$C_{1-6}$ alkylcarbonyl: —COMe;
$C_{1-6}$ alkoxycarbonyl: —COOMe;
$C_{1-6}$ alkoxycarbonyl $C_{1-6}$ alkyl: —$CH_2COOMe$;
$C_{1-6}$ alkylaminocarbonyl: —CONHMe;
di $C_{1-6}$ alkylaminocarbonyl: —$CONMe_2$ or —CO(1-pyrrolidinyl);
—$(CH_2)_p$— when cyclized onto Ar is as follows:

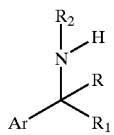

A preferred group of compounds is when R is $C_{1-6}$ alkyl, $C_{1-6}$ alkoxycarbonyl, $C_{1-6}$ alkylcarbonyl, or hydroxy $C_{1-6}$ alkyl. A particularly preferred group of compounds is when R is $C_{1-6}$ alkyl. Most preferably R is ethyl.

An example of $R_1$ and $R_2$ as $C_{1-6}$ alkyl is methyl, ethyl, n-propyl, isopropyl, n-butyl, and the like; an example of $R_1$ together with R forming a group —$(CH_2)_q$— is spirocyclopentane. Preferably $R_1$ and $R_2$ are each hydrogen or $C_{1-6}$ alkyl. Most preferably, $R_1$ and $R_2$ are each hydrogen.

Examples of $R_3$ and $R_4$ are independently hydrogen, methyl, ethyl, n-propyl, n-butyl, methoxy, hydroxy, chlorine, fluorine, bromine, 2-(dimethylamino)ethoxy, dimethylaminopropoxy, dimethylaminoacetylamino, acetylamino, dimethylaminomethyl and phenyl. Preferably $R_3$ is hydrogen, hydroxy, halogen, $C_{1-6}$ alkoxy, $C_{1-6}$ alkyl. Preferably $R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino. Most preferably, $R_3$ is hydrogen. Most preferably $R_4$ is $C_{1-6}$ alkoxy or hydroxy. Particularly preferable is when $R_4$ is hydroxy.

Examples of $R_5$ are cyclohexyl, phenyl optionally substituted as defined for Ar above; examples of $R_5$ as a heterocyclic group are furyl, thienyl, pyrryl, thiazolyl, benzofuryl and pyridyl. Preferably $R_5$ is phenyl, thienyl, furyl, pyrryl and thiazolyl. Most preferably $R_5$ is phenyl.

Preferred compounds of formula (I) made by the process of the invention are wherein, Ar is phenyl, optionally substituted by $C_{1-6}$ alkyl or halogen; thienyl or a $C_{5-7}$ cycloalkdienyl group; R is $C_{1-6}$ alkyl, $C_{1-6}$ alkoxycarbonyl, $C_{1-6}$ alkylcarbonyl, hydroxy $C_{1-6}$ alkyl; $R_1$ and $R_2$ are each hydrogen or $C_{1-6}$ alkyl; $R_3$ is hydrogen, hydroxy, halogen, $C_{1-6}$ alkoxy, $C_{1-6}$ alkyl; $R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino; and $R_5$ is phenyl, thienyl, furyl, pyrryl and thiazolyl.

A more preferred compound made by the process of this invention is wherein, Ar is phenyl; R is ethyl; $R_1$ and $R_2$ are each hydrogen; $R_3$ is hydrogen; $R_4$ is hydroxy; and $R_5$ is phenyl.

The term "alkyl" as used herein at all occurrences means both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like.

The term "alkoxy" is used herein at all occurrences to mean a straight or branched chain radical of 1 to 8 carbon atoms, unless the chain length is limited thereto, bonded to an oxygen atom, including, but not limited to, methoxy, ethoxy, n-propoxy, isopropoxy, and the like.

The term "halogen" is used herein at all occurrences to mean chloro, fluoro, iodo and bromo.

The term "cycloalkyl" is used herein at all occurrences to mean cyclic radicals, preferably of 3 to 7 carbons, including but not limited to cyclopropyl, cyclopentyl, cyclohexyl, and the like.

The terms "aryl" or "heteroaryl" are used herein at all occurrences to mean substituted and unsubstituted aromatic ring(s) or ring systems which may include bi- or tri-cyclic systems and heteroaryl moieties, which may include, but are not limited to, heteroatoms selected from O, N, or S. Representative examples include, but are not limited to, phenyl, benzyl, naphthyl, pyridyl, quinolinyl, thiazinyl, and furanyl.

The term "optionally substituted" is used herein at all occurrences to mean that the moiety may be substituted or not, and if it is substituted, one or more hydrogen on each moiety is replaced with one or more substituents, each substituent being chosen independently from hydroxy, halogen, $C_{1-6}$ alkoxy or $C_{1-6}$ alkyl, as defined above.

A particularly preferred compound of formula (I) is (–)-(S)-N-(α-ethylbenzyl)-3-hydroxy-2-phenylquinoline-4-carboxamide. A preferred pharmaceutically active salt of formula (I) is (–)-(S)-N-(α-ethylbenzyl)-3-hydroxy-2-phenylquinoline-4-carboxamide, hydrochloride.

The compounds described herein may have asymmetric centers. Unless otherwise indicated, all chiral, diasteriomeric and racemic forms are included in the present invention. As is often the case, optimal therapeutic activity is provided only by one configuration of the two chiral centers. It is therefore desirable to produce this material in a form which is highly enriched in only one absolute configuration of the chiral centers. It is well known in the art how to prepare optically active compounds, such as by resolution of the racemic mixture, or by synthesis from optically active starting materials.

Isatin and substituted isatins of formula (III) are commercially available, or are made by methods known in the art, such as Marvel, et al., Org. Synth. Collect.

Vol. I, 1941, p. 327.

Compounds of formula (II) and related formula (II') are also known, commercially available, or can be made by known methods. See, e.g., Normant et al., *Synthesis*, 1975, pp. 805–807. A particularly useful compound of formula (II) is α-acetoxy acetophenone, purchased from Lancaster Synthesis Company.

Compounds of formula (IV) and related formula (IV') are known or are made by known methods including those disclosed in Marshall et al., Cinchoninic Acid Derivatives, Vol. 95, 1949, pp. 185–190; U.S. Pat. Nos. 2,749,347, issued Jun. 5, 1956; and 2,776,290, issued Jan. 1, 1957. The procedure described in Marshall was modified herein by using LiOH as a preferable base over NaOH.

The reactions of the synthetic methods disclosed herein are carried out in a suitable solvent, which is a solvent substantially nonreactive (except where required as a reagents as well) with the reactants, the intermediates or products at the temperatures at which the reactions are performed. Suitable solvents for coupling a compound of formula (III) with a compound of formula (II) are water, $C_{1-4}$ alcohols, dimethyl sulfoxide ("DMSO") and dimethylformamide ("DMF"). Water is preferred.

Suitable aqueous bases used in this coupling step are lithium hydroxide, sodium hydroxide, potassium hydroxide, calcium hydroxide and barium hydroxide. Lithium hydroxide is preferred. Suitably the base is present in an amount between 2 and 6 equivalents, preferably 3 to 5 equivalents, and most preferably 4 equivalents of base is used.

The compound of formula (III) is added to aqueous base which has been heated to a temperature between about 40 and 70° C., preferably between about 50 and 60° C. The ring of the compound of formula (III) opens upon reaction with aqueous base. The compound of formula (II) is then added, with an exotherm of about 15° C. After the addition of the compound of formula (II) is complete, the temperature of the resulting reaction mixture is raised up to a temperature between about 40° C. and about 110° C., preferably up to about 80° C., for an appropriate time period (up to about three hours) or until completion of the coupling provides a compound of formula (IV).

The compound of formula (IV) is isolated prior to performing the next step in the process. It is important that the next step be conducted under anhydrous conditions since the carbonyl-activating agent, e.g., $SOCl_2$, oxalyl chloride, DCC, $POCl_3$, $COCl_2$, etc., is hydrolytically unstable and would be destroyed by water. A preferred carbonyl-activating agent for use in the methods herein is thionyl chloride. Suitable solvents for use in this step are aprotic solvents, including, but not limited to, polar aprotic organic solvents. More specifically, solvents useful herein include, but are not limited to, ethyl acetate, toluene, tetrahydrofuran, or acetonitrile. A preferred solvent for use herein is ethyl acetate.

Suitable bases useful in this step of the process include amine bases, particularly tertiary amine bases. Preferred amine bases are triethyl amine and diisopropylethyl amine. Most preferred is triethyl amine. Suitably, at least 3 equivalents of the amine base are used in the instant reaction process.

After the addition of the base to the compound of formula (IV), the reaction mixture is cooled to a temperature below 5° C. Preferably the temperature ranges between about −2 and 2° C. The carbonyl-activating agent (e.g., thionyl chloride, $COCl_2$ and $POCl_3$) is added and then the reaction mixture is allowed to slowly (about 1 hour) warm to room temperature (about 25° C.), at which point a compound of formula (V) or formula (Va), shown below, is added. Compounds of formula (V) are commercially available from BASF, Celgene, Inc., and Zeeland Chemical Co., or can be made using methods known in the art, e.g., Itsuno, S. et al., *J. Chem. Soc., Perkin Trans. I*, 1985, p. 2039; Burk, M. J. et al., *J. Am. Chem. Soc.*, 1996, 118, p. 5142; and Beak, P. et al., *J. Am. Chem. Soc.*, 1996, 118, p. 3757. A particularly preferred compound of formulae (V) or (Va) for use in the method herein is (S)-1-phenyl propylamine.

Again, without being bound to any particular theory, an investigation of the reaction sequences to determine the actual coupling species revealed, by thin-layer chromatography, three major components in the reaction mixture formed prior to addition of the compound of formula (V). When isolated, the three components were consistent with (1) a compound of formula (VII); (2) a compound of formula (VIII), wherein n is 1; and (3) a compound of formula (VIII), wherein n is 3. Reaction of each of the three components with a compound of formula (V) under conditions as defined herein, each provided the desired compound of formula (I). Also isolated was the trimer of the compound of formula (VIII), however, even under forced conditions, this compound did not provide the desired compound of formula (I).

While no spectral evidence exists for formation during the coupling of compound (IV) and compound (V) of the following intermediate:

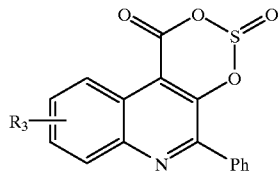

speculation leads one to predict that the tertiary amine base catalyzes a rapid conversion of the putative intermediate to the coupling species of formula (VIII). Upon addition of the compound of formula (V) at room temperature, the compound of formula (VIII), wherein n is 1, reacts to produce a further intermediate of formula (VI), which, upon heating to temperatures between 50 and 60° C., reacts with another molecule of the compound of formula (V) ultimately to produce two molecules of the desired compound of formula (I). By pushing the intermediates to react with the compound of formula (V), the yield of desired product increases. In addition, by converting the side-product of formula (VI) to product, the yield increases, and the need for chromatographic removal of this side-product is eliminated.

A preferred sub-group of compounds within the scope of formula (I) are the compounds of formula (Ia):

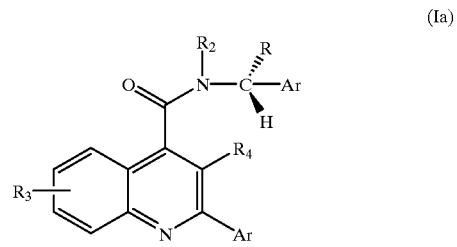

wherein:

Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, an optionally substituted phenyl group or a phenyl $C_{1-6}$ alkyl group, an optionally substituted five-membered heteroaromatic ring comprising up to four heteroatom selected from O and N, hydroxy $C_{1-6}$ alkyl, di $C_{1-6}$ alkylaminoalkyl, $C_{1-6}$ acylaminoalkyl, $C_{1-6}$ alkylcarbonyl, carboxy, $C_{1-6}$ alkoxycarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl; or is a group —$(CH_2)_p$— when cyclized onto Ar, where p is 2 or 3;

$R_2$ is hydrogen or $C_{1-6}$ linear or branched alkyl; and $R_3$ and $R_4$, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —$O(CH_2)_r$—$NT_2$, in which r is 2, 3, or 4 and T is $C_{1-6}$ alkyl or it forms a heterocyclic group

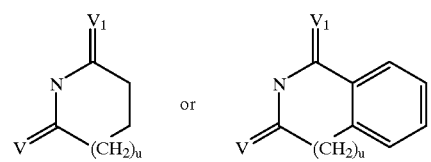

in which V and $V_1$ are hydrogen and u is 0, 1 or 2; —$O(CH_2)_s$—$OW_2$ in which s is 2, 3, or 4 and W is $C_{1-6}$ alkyl; hydroxyalkyl, mono-or di-alkylaminoalkyl, acylamino, alkylsulphonylamino, aminoacylamino, mono- or di-alkylaminoacylamino; with up to four $R_3$ substituents being present in the quinoline nucleus;

which can be prepared by a method comprising:

1) adding a compound of formula (III):

Formula (III)

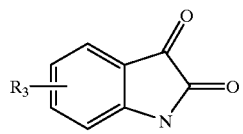

to base in a suitable solvent, to form a first reaction mixture, adding to the first reaction mixture a compound of formula (IIa):

Formula (IIa)

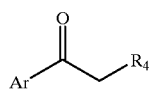

to form a second reaction mixture, and heating the second reaction mixture to form a compound of formula (IVa):

Formula (IVa)

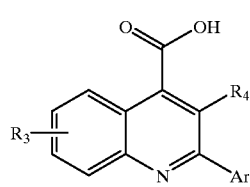

2) isolating the compound of formula (IVa) and then reacting the compound of formula (IVa), in a suitable solvent, with a base to form a third reaction mixture, cooling the third reaction mixture, and adding a carbonyl-activating agent to form a fourth reaction mixture;

3) adding a compound of formula (Va):

Formula (Va)

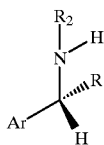

to the fourth reaction mixture to form a fifth reaction mixture;

4) heating the fifth reaction mixture; and 5) optionally converting the compound of formula (Ia) to a pharmaceutically acceptable salt thereof, wherein Ar, R, $R_1$, $R_2$, $R_3$, $R_4$, and $R_5$ as used in a compound of formulae (IIa), and (IVa) through (VIa) are as defined for a compound of formula (Ia).

For a compound of formula (Ia) preferred embodiments are as follows.

Suitably Ar is phenyl, optionally substituted by $C_{1-6}$ alkyl or halogen; thienyl, furyl, pyrryl, thiazolyl, or a $C_{5-7}$ cycloalkdienyl group. Preferably Ar is phenyl.

Suitably R is $C_{1-6}$ alkyl, $C_{1-6}$ alkoxycarbonyl, $C_{1-6}$ alkylcarbonyl, or hydroxy $C_{1-6}$ alkyl. Preferably R is $C_{1-6}$ alkyl, most preferably ethyl.

Suitably $R_2$ is hydrogen or $C_{1-6}$ alkyl. Preferably $R_2$ is hydrogen.

Suitably $R_3$ is hydrogen, hydroxy, halogen, $C_{1-6}$ alkoxy or $C_{1-6}$ alkyl. Preferably $R_3$ is hydrogen.

Suitably $R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino. Preferably $R_4$ is $C_{1-6}$ alkoxy or hydroxy, most preferably hydroxy.

A preferred group of compounds of formula (Ia) made by the process of this invention are wherein, Ar is phenyl, optionally substituted by $C_{1-6}$ alkyl or halogen; thienyl, furyl, pyrryl, thiazolyl, or a $C_{5-7}$ cycloalkdienyl group; R is $C_{1-6}$ alkyl, $C_{1-6}$ alkoxycarbonyl, $C_{1-6}$ alkylcarbonyl, or hydroxy $C_{1-6}$ alkyl; $R_2$ is hydrogen or $C_{1-6}$ alkyl; $R_3$ is hydrogen, hydroxy, halogen, $C_{1-6}$ alkoxy, $C_{1-6}$ alkyl; and $R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino.

A more preferred group of compounds of formula (Ia) made by the process of this invention are wherein, Ar is phenyl; R is $C_{1-6}$ alkyl; $R_2$ is hydrogen; $R_3$ is hydrogen; and $R_4$ is $C_{1-6}$ alkoxy or hydroxy.

A very preferred compound of formula (Ia) is wherein, Ar is phenyl; R is ethyl; $R_2$ is hydrogen; $R_3$ is hydrogen; and $R_4$ is hydroxy.

Optically pure compounds of formula (Va) are commercially available from BASF, Celgene, Inc., and Zeeland Chemical Co., or can be made by methods known in the art, e.g., Itsuno, S. et al., *J. Chem. Soc., Perkin Trans.* I, 1985, p. 2039; Burk, M. J. et al., *J. Am. Chem. Soc.,* 1996, 118, p. 5142; and Beak, P. et al., *J. Am. Chem. Soc.,* 1996, 118, p. 3757. If the racemic mixture of formula (V) is used, then the racemate of the final product of formula (I) is made. Separation of the optically active enantiomers is accomplished by known methods, e.g., HPLC.

Suitable solvents for coupling a compound of formula (III) with a compound of formula (IIa) are water, $C_{1-4}$ alcohols, dimethyl sulfoxide ("DMSO") and dimethylformamide ("DMF"). Water is preferred.

Suitable aqueous bases used in this coupling step are lithium hydroxide, sodium hydroxide, potassium hydroxide, calcium hydroxide and barium hydroxide. Lithium hydroxide is preferred. Suitably the base is present in an amount between 2 and 6 equivalents, preferably 3 to 5 equivalents, and most preferably 4 equivalents of base is used.

The compound of formula (III) is added to aqueous base which has been heated to a temperature between about 40 and 70° C., preferably between about 50 and 60° C. The ring of the compound of formula (III) opens upon reaction with aqueous base. The compound of formula (IIa) is then added, with an exotherm of about 15° C. After the addition of the compound of formula (IIa) is complete, the temperature of the resulting reaction mixture is raised up to a temperature between about 40° C. and about 110° C., preferably up to about 80° C., for an appropriate time period (up to about three hours) or until completion of the coupling provides a compound of formula (IVa).

The compound of formula (IVa) is isolated prior to performing the next step in the process. It is important that the next step be conducted under anhydrous conditions since the carbonyl-activating agent, e.g., $SOCl_2$, oxalyl chloride, DCC, $POCl_3$, $COCl_2$, etc., is hydrolytically unstable and would be destroyed by water. A preferred carbonyl-activating agent for use in the methods herein is thionyl chloride. Suitable solvents for use in this step are aprotic solvents, including, but not limited to, polar aprotic organic solvents. More specifically, solvents useful herein include, but are not limited to, ethyl acetate, toluene, tetrahydrofuran, or acetonitrile. A preferred solvent for use herein is ethyl acetate.

Suitable bases useful in this step of the process include amine bases, particularly tertiary amine bases. Preferred amine bases are triethyl amine and diisopropylethyl amine. Most preferred is triethyl amine. Suitably, at least 3 equivalents of the amine base are used in the instant reaction process.

After the addition of the base to the compound of formula (IVa), the reaction mixture is cooled to a temperature below 5° C. Preferably the temperature ranges between about −2 and 2° C. The carbonyl-activating agent is added and then the reaction mixture is allowed to slowly (about 1 hour) warm to room temperature (about 25° C.), at which point a compound of formula (Va), shown below, is added. A particularly preferred compound of formula (Va) for use in the method herein is (S)-1-phenyl propylamine.

It will be under stood that the fifth reaction mixture comprises the compound of formula (I) and a compound of formula (VIa):

Formula (VI)

Upon heating the fifth reaction mixture, the compound of formula (VI) is converted to desired product.

This invention also provides a method for preparing (−)-(S)-N-(α-ethylbenzyl)-3-hydroxy-2-phenylquinoline-4-carboxamide comprising:

1) adding isatin to base in a suitable solvent to form a first reaction mixture, adding to the first reaction mixture an α-acetoxy ketone to form a second reaction mixture, and heating the second reaction mixture to form an α-hydroxy acid;

2) reacting the α-hydroxy acid, in a suitable solvent, with a tertiary amine base to form a third reaction mixture, cooling the third reaction mixture, and adding a carbonyl-activating agent to form a fourth reaction mixture;

3) adding a primary or secondary amine to the fourth reaction mixture to form a fifth reaction mixture;

4) heating the fifth reaction mixture; and 5) optionally converting (−)-(S)-N-(α-ethylbenzyl)-3-hydroxy-2-phenylquinoline-4-carboxamide to a pharmaceutically acceptable salt.

Suitably, for step (1) the base is aqueous base, preferably LiOH.

Preferably, the α-acetoxy ketone is α-acetoxy acetophenone.

Preferably, the α-hydroxy acid formed in step (1) is 3-hydroxy-2-phenylquinoline-4-carboxylic acid.

Preferably, the tertiary amine base of step (2) is triethyl amine.

Preferably, the carbonyl-activating agent of step (2) is thionyl chloride.

Preferably, the amine of step (3) is (S)-1-phenyl propylamine.

The fifth reaction mixture suitably comprises (−)-(S)-N-(α-ethylbenzyl)-3-hydroxy-2-phenylquinoline-4-carboxamide and (S)-2-Phenyl-4-[[(1-phenylpropyl)amino]carbonyl]-3-quinolinyl-3-hydroxy-2-phenyl-4-quinoline-carboxylate.

A particularly preferred pharmaceutically acceptable salt is the novel (−)-(S)-N-(α-ethylbenzyl)-3-hydroxy-2-phenylquinoline-4-carboxamide, hydrochloride salt. The hydrochloride salt is prepared according to the Examples described below.

The product of the above defined reaction may be transformed to other intermediate products which may be active compounds of formula (I) or formula (Ia) or which may be useful in producing the compounds of formula (I) and formula (Ia) by well known methods.

The present invention also provides for a method for preparing (−)-(S)-N-(α-ethylbenzyl)-3-hydroxy-2-phenylquinoline-4-carboxamide comprising:

1) reacting 3-hydroxy-2-phenylquinoline-4-carboxylic acid, in a suitable solvent, with triethyl amine to form a first reaction mixture, cooling the first reaction mixture, and adding thionyl chloride to form a second reaction mixture comprising 6,14,22,30-Tetraphenyl-[1,5,9,13]tetraoxahexadecino[2,3-c:6,7-c':10,11-c":14,15-c'"]tetraquinoline-8,16,24,32-tetrone and Ethyl 3-acetoxy-2-phenylquinoline-4-carboxylate;

2) adding (S)-1-phenyl propylamine to the second reaction mixture to form a third reaction mixture comprising (−)-(S)-N-(α-ethylbenzyl)-3-hydroxy-2-phenylquinoline-4-carboxamide and (S)-2-Phenyl-4-[[(1-phenylpropyl)amino]carbonyl]-3-quinolinyl-3-hydroxy-2-phenyl-4-quinoline-carboxylate;

3) heating the third reaction mixture; and 4) optionally converting (−)-(S)-N-(α-ethylbenzyl)-3-hydroxy-2-phenylquinoline-4-carboxamide to a pharmaceutically acceptable salt.

It will be understood that reacting 3-hydroxy-2-phenylquinoline-4-carboxylic acid can be made by procedures described above for formula (IV) and formula (IVa).

The present invention also provides novel compounds of formula (VII):

Formula (VII)

wherein:

Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N; and $R_3$ is hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —O(CH$_2$)$_r$—NT$_2$, in which r is 2, 3, or 4 and T is $C_{1-6}$ alkyl or it forms a heterocyclic group in which V and $V_1$ are hydrogen and u is 0, 1 or 2;

—O(CH$_2$)$_s$—OW$_2$ in which s is 2, 3, or 4 and W is $C_{1-6}$ alkyl; hydroxyalkyl, mono-or di-alkylaminoalkyl, acylamino, alkylsulphonylamino, aminoacylamino, mono- or di-alkylaminoacylamino; with up to four $R_3$ substituents being present in the quinoline nucleus; and R'$_4$ is OH or OAc; which are useful as intermediates for the synthesis of pharmaceutically active quinoline compounds of formula (I) or pharmaceutically acceptable salts thereof, particularly of (−)-(S)-N-(α-ethylbenzyl)-3-hydroxy-2-phenylquinoline-4-carboxamide and its hydrochloride salt.

For a compound of formula (VII) preferred embodiments are as follows.

Suitably Ar is phenyl, optionally substituted by hydroxy, halogen, $C_{1-6}$ alkoxy or $C_{1-6}$ alkyl; thienyl or a $C_{5-7}$ cycloalkdienyl group. Preferably when Ar is substituted phenyl, the substituents are $C_{1-6}$ alkyl or halogen. Examples of Ar as a heterocyclic group are thienyl and pyridyl. Examples of Ar as a $C_{5-7}$ cycloalkdienyl group is cyclohexadienyl.

Most preferably Ar is phenyl.

Examples of $R_3$ are methyl, ethyl, n-propyl, n-butyl, methoxy, hydroxy, amino, chlorine, fluorine, bromine, 2-(dimethylamino)ethoxy, dimethylaminopropoxy, dimethylaminoacetylamino, acetylamino, dimethylaminomethyl and phenyl. Suitably $R_3$ is hydrogen, hydroxy, halogen, $C_{1-6}$ alkoxy, or $C_{1-6}$ alkyl.

Preferably $R_3$ is hydrogen.

Suitably $R'_4$ is acetoxy or hydroxy.

An especially preferred compound is Ethyl 3-acetoxy-2-phenylquinoline-4-carboxylate, i.e., a compound of formula (VII), wherein Ar is phenyl, $R_3$ is hydrogen, and $R'_4$ is OAc.

The novel intermediates of formula (VII) are prepared using a preferred sub-group of compounds within the scope of formula (I), formula (II), and formula (IV), i.e., the compounds of formulae (II') and (IV'). The method for making intermediates of formula (VII) comprises:

1) adding a compound of formula (III):

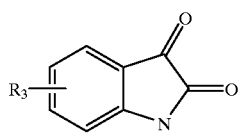

Formula (III)

to at least 2 to 6 equivalents, most preferably 4 equivalents, of aqueous base, preferably lithium hydroxide, sodium hydroxide, potassium hydroxide, calcium hydroxide and barium hydroxide, most preferably lithium hydroxide, in a suitable solvent, e.g., water, $C_{1-4}$ alcohols, DMSO and DMF, preferably water, to form a first reaction mixture, adding to the first reaction mixture a compound of formula (II'):

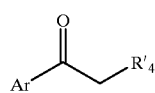

Formula (II')

to form a second reaction mixture, and heating the second reaction mixture to form a compound of formula (IV'):

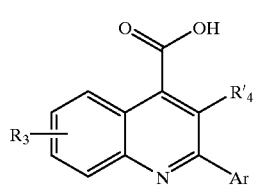

Formula (IV')

2) isolating the compound of formula (IV') and then reacting the compound of formula (IV'), in a suitable solvent, e.g., ethyl acetate with a base, suitably at least 3 equivalents of an amine base, e.g., triethyl amine and diisopropylethyl amine, to form a third reaction mixture, cooling the third reaction mixture below about 5° C., preferably between −2 and 2° C., and adding a carbonyl-activating agent, e.g., thionyl chloride to form a fourth reaction mixture comprising a compound of formula (VII), wherein $R_3$, $R'_4$, and Ar are as defined above for formula (VII).

The present invention further provides novel compounds of formula (VIII):

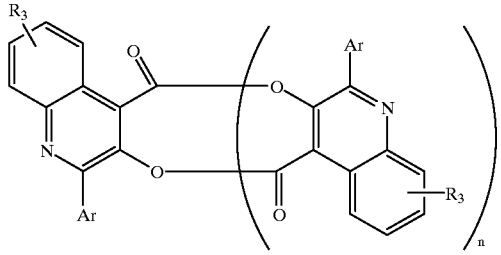

Formula (VIII)

wherein:

Ar and $R_3$ are as defined for a compound of formula (I) as claimed in claim 1; and n is 1 or 3.

The intermediate of formula (VIII) is prepared by the process described above for preparing the intermediate of formula (VII) except, as one of skill in the art would expect, the mechanism for producing the two intermediates is not likely the same. A preferred intermediate of formula (VIII) is wherein n is 1, i.e., 6,14-diphenyl-[1,5]dioxocino[2,3-c:6,7-c']diquinoline-8,16-dione. Another preferred intermediate of formula (VIII) is wherein n is 3, i.e., 6,14,22,30-Tetraphenyl-[1,5,9,13]tetraoxahexadecino [2,3-c:6,7-c':10,11-c":14,15-c'"]tetraquinoline-8,16,24,32-tetrone.

The following examples are intended in no way to limit the scope of this invention. The nomenclature and abbreviations common to the chemical art are used in the examples. Melting points are uncorrected. Liquid chromatograph was conducted on a Zorbax SB C18 column, 3.5 micron (0.46×7.5 cm) with a flow rate of 1.0 mL/min and detection at 360 nm. The solvents were 40:60:0.1 of Acetonitrile:Water:Trifluoroacetic acid. The chiral purity of the products were determined by chiral HPLC conducted on a Chiralpak AD column, 10 micron (0.46 ×25 cm) with a flow rate of 1.0 mL/min and detection at 360 nm. The solvents were 85:15 n-Hexane:Ethanol. All $^{13}$C NMR (carbon magnetic resonance) and $^1$H NMR (proton magnetic resonance) spectra were obtained using a Bruker Instrument in Dimethyl Sulfoxide-$d_6$. $^{13}$C spectra were run using the GASPE (Gated-Spin Echo) pulse sequence.

EXAMPLES

Example 1: Synthesis of 3-hydroxy-2-phenylquinoline-4-carboxylic acid

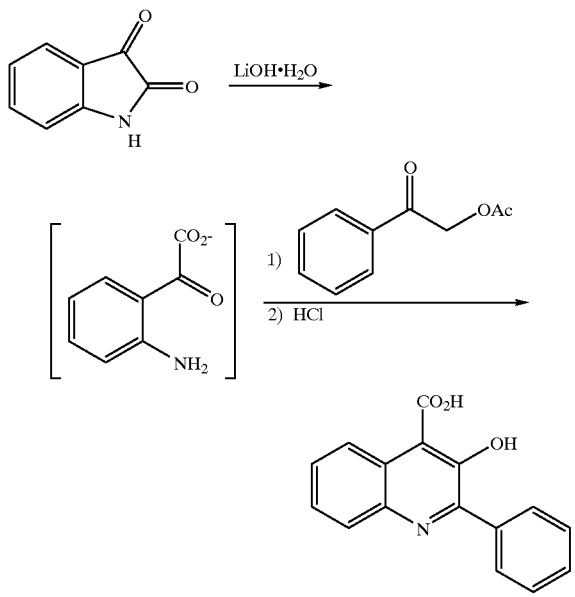

A 1 L round-bottomed flask was charged with 360 mL of water and LiOH.H$_2$O (34.3 g, 800 mmol) and stirred at 50–60° C. Isatin (30 g, 200 mmol) was added and the reaction stirred for 30 minutes at 50–60° C. The (α-acetoxy acetophenone (40.95 g, 230 mmol, 1.15 equiv.) was added as a solid in one portion and the solution heated at 80–85° C. until <5% by PAR isatin remains as shown by HPLC (typically 3 hours). The reaction was cooled to room temperature, diluted with water (90 mL) and tert-butyl methyl ether ("TBME") (210 mL) and transferred to a separatory funnel. The mixture was shaken well and the aqueous layer drained into an Ehrlenmeyer flask. The aqueous layer was acidified to pH=3.0–3.5 using conc. HCl (~61 mL) and monitored with a pH meter. The suspension of yellow solid was heated to 60–70° C., and held at that temperature for 5–10 minutes and filtered through a Buchner funnel. The flask was rinsed with 90 mL of water at 60–70° C. and the filter cake was washed with this rinse. The solid was suction dried for 10 minutes and charged back to the 1 L flask. The flask was charged with 600 mL of water, the suspension heated to 60–70° C., held there for 10 minutes, and filtered through a Buchner funnel. The flask was rinsed with 150 mL of water at 60–70° C. and the filter cake washed with this rinse. The filter cake was dried in a vacuum oven at 80–90° C. and <1 mm Hg. After drying to constant weight, the product 3-hydroxy-2-phenylquinoline-4-carboxylic acid (82%) was obtained as a bright yellow solid: mp 206° C.; IR (cm$^{-1}$) 3430, 2600, 1634; $^1$H NMR (300 MHz, DMSO-d$_6$) δ8.75 (1H, δ, J=8.2 Hz), 8.01 (3H, m), 7.59 (5H, m); $^{13}$C NMR (75 MHz, DMSO-d$_6$) δ171.03, 153.98, 151.38, 139.68, 135.62, 129.60, 129.38, 128.27, 127.83, 126.27, 125.22, 124.54, 115.26.

Example 2: Synthesis of (−)-(S)-N-(α-ethylbenzyl)-3-hydroxy-2-phenylquinoline-4-carboxamide, hydrochloride

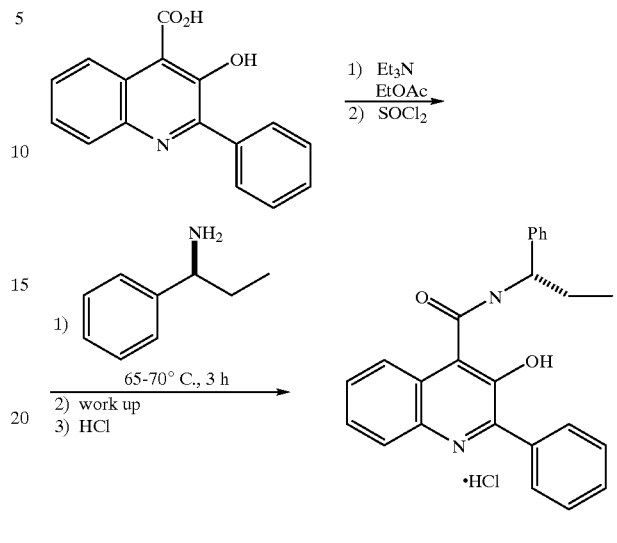

A suitable reactor vessel was charged with 265 g (1 Mol) of 3-hydroxy-2-phenylquinoline-4-carboxylic acid and ethyl acetate (25 volumes, 5.98 Kg, 6.63 L). The yellow slurry was heated at 30–40° C., and the ethyl acetate distilled off under high vacuum until 15 volumes of solvent remained in the still pot. After vacuum distillation, the yellow slurry was cooled to 20–25° C. Added triethylamine (3.0 Mol, 0.31 Kg, 0.42 L) to afford a dark orange solution. Cooled the solution to −2° C. and slowly added thionyl chloride (1.05 Mol, 0.13 Kg, 0.080 L), over approx. 30 minutes, keeping the solution temperature less than 2° C. After complete addition, the tan slurry was stirred at 25° C. for 1 hour. Added (S)-1-phenyl-n-propylamine (1.1 Mol, 0.16 Kg, 0.17 L) and heated at 65–70° C. for about 3 hours. After 3 hours at 65–70° C., cooled the reaction to 20–25° C. The reactor was charged with ethyl acetate (10 volumes, 2.39 Kg, 2.65 L) and stirred for 5–10 minutes. Added deionized water (15 volumes, 3.98 Kg, 3.98 L). Stirred the reactor contents at ambient temperature for 5 minutes and then separated the phases. Washed the organic layer with 0.5 M aq. citric acid (2×10 volumes, 2×2.8 Kg, 2×2.6 L) followed by deionized water (5 volumes, 1.3 Kg, 1.3 L). At this point, a sample of the organic phase can be removed and assayed by HPLC to determine the presence and content of the freebase form of the desired product. (Note: Typical solution yields range from 80–84% and one can proceed assuming an 80% solution yield). Added toluene (15 volumes, 3.44 Kg, 3.98 L) and concentrated the solution via vacuum distillation until a final reactor volume of 2.2 L was obtained (this represents 7 volumes of solvent remaining based on freebase available). The reactor was charged with IPA (isopropyl amine) (3 volumes based on freebase available), 0.72 Kg, 0.92 L) and the reactor contents warmed to 70° C. to afford a clear solution. To the solution, 58.4 g (2 equiv.) of HCl (g) was bubbled in slowly to precipitate the desired product. The precipitate was cooled to 0° C. and held for about 1 hour. The product was collected by suction filtration. The reaction flask was rinsed with TBME (4 volumes, 0.90 Kg, 1.22 L) and the TBME used as a rinse to wash the filter cake. This washing was repeated with an additional portion of TBME (4 volumes, 0.90 Kg, 1.22 L). The product was dried to a constant weight in a vacuum oven at 70° C./<1.0 mm Hg.

The yield of desired product was 301 g, affording a 72% yield of a light beige product: mp=179–180° C., IR (cm$^{-1}$) 2450, 1627, 1322; $^1$H NMR (300 MHz, DMSO-d$_6$) δ9.20 (1H, d, J=8.2 Hz), 8.19 (1H, d, J=8.4 Hz), 7.96 (2H, m), 7.71 (1H, m), 7.60 (5H, m), 7.44 (2H, m), 7.37 (2H, m), 7.27 (1H, m), 5.02 (1H, q, J=7.5 Hz), 1.81 (2H, m), 0.94 (3H, t, J=7.2 Hz). $^{13}$C NMR (100.625 Mhz) δ169.8, 151.7, 144.8, 143.3, 139.7, 134.9, 131.3, 129.9, 129.8, 128.3, 128.2, 128.0, 126.8, 126.7, 126.5, 125.7, 123.9, 55.0, 29.3, 11.1.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. A method for preparing a compound of formula (I):

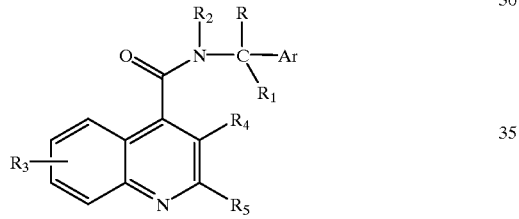

Formula (I)

or a pharmaceutically acceptable salt form thereof, wherein:
Ar is an optionally substituted phenyl group, or a naphthyl or C$_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N;
R is linear or branched C$_{1-8}$ alkyl, C$_{3-7}$ cycloalkyl, C$_{4-7}$ cycloalkylalkyl, an optionally substituted phenyl group or a phenyl C$_{1-6}$ alkyl group, an optionally substituted five-membered heteroaromatic ring comprising up to four heteroatom selected from O and N, hydroxy C$_{1-6}$ alkyl, di C$_{1-6}$ alkylaminoalkyl, C$_{1-6}$ acylaminoalkyl, C$_{1-6}$ alkoxyalkyl, C$_{1-6}$ alkylcarbonyl, carboxy, C$_{1-6}$ alkoxycarbonyl, C$_{1-6}$ alkoxycarbonyl C$_{1-6}$ alkyl, aminocarbonyl, C$_{1-6}$ alkylaminocarbonyl, di C$_{1-6}$ alkylaminocarbonyl; or is a group —(CH$_2$)$_p$— when cyclized onto Ar, where p is 2 or 3;
R$_1$ and R$_2$, which may be the same or different, are independently hydrogen or C$_{1-6}$ linear or branched alkyl, or together form a —(CH$_2$)$_n$— group in which n represents 3, 4, or 5; or R$_1$ together with R forms a group —(CH$_2$)$_q$—, in which q is 2, 3,4 or 5;
R$_3$ and R$_4$, which may be the same or different, are independently hydrogen, C$_{1-6}$ linear or branched alkyl, C$_{1-6}$ alkenyl, aryl, C$_{1-6}$ alkoxy, hydroxy, halogen, nitro, cyano, carboxy, carboxamido, sulphonamido, trifluoromethyl, amino, mono- and di-C$_{1-6}$ alkylamino, —O(CH$_2$)$_r$—NT$_2$, in which r is 2, 3, or 4 and T is C$_{1-6}$ alkyl or it forms a heterocyclic group

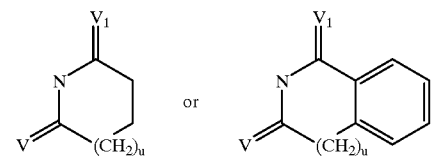

in which V and V$_1$ are hydrogen and u is 0, 1 or 2;
—O(CH$_2$)$_s$—OW$_2$ in which s is 2, 3, or 4 and W is C$_{1-6}$ alkyl; hydroxyalkyl, mono- or di-alkylaminoalkyl, acylamino, alkylsulphonylamino, aminoacylamino, mono- or di-alkylaminoacylamino; with up to four R$_3$ substituents being present in the quinoline nucleus;
or R$_4$ is a group —(CH$_2$)$_t$— when cyclized onto R$_5$ as aryl, in which t is 1, 2, or 3; and
R$_5$ is branched or linear C$_{1-6}$ alkyl, C$_{3-7}$ cycloalkyl, C$_{4-7}$ cycloalkylalkyl, optionally substituted aryl, wherein the optional substituent is one of hydroxy, halogen, C$_{1-6}$ alkoxy or C$_{1-6}$ alkyl, or an optionally substituted single or fused ring heterocyclic group, having aromatic character, containing from 5 to 12 ring atoms and comprising up to four hetero-atoms in the or each ring selected from S, O, N; comprising:

1) adding a compound of formula (III):

Formula (III)

to base in a suitable solvent, to form a first reaction mixture, adding to the first reaction mixture a compound of formula (II):

Formula (II)

to form a second reaction mixture, and heating the second reaction mixture to form a compound of formula (IV):

Formula (IV)

2) isolating the compound of formula (IV) and then reacting the compound of formula (IV), in a suitable solvent, with a base to form a third reaction mixture, cooling the third reaction mixture, and adding thionyl chloride to form a fourth reaction mixture;

3) adding a compound of formula (V):

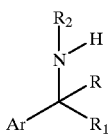

Formula (V)

to the fourth reaction mixture to form a fifth reaction mixture;

4) heating the fifth reaction mixture; and 5) optionally converting the compound of formula (I) to a pharmaceutically acceptable salt thereof, wherein Ar, R, $R_1$, $R_2$, $R_3$, $R_4$, and $R_5$ as used in a compound of formulae (II) through (V) are as defined for a compound of formula (I).

2. The method as claimed in claim 1, wherein for the compound of formula (I):

Ar is phenyl, optionally substituted by $C_{1-6}$ alkyl or halogen; thienyl or a $C_{5-7}$ cycloalkdienyl group;

R is $C_{1-6}$ alkyl, $C_{1-6}$ alkoxycarbonyl, $C_{1-6}$ alkylcarbonyl, hydroxy $C_{1-6}$ alkyl;

$R_1$ and $R_2$ are each hydrogen or $C_{1-6}$ alkyl;

$R_3$ is hydrogen, hydroxy, halogen, $C_{1-6}$ alkoxy, $C_{1-6}$ alkyl;

$R_4$ is hydrogen, $C_{1-6}$ alkyl, $C_{1-6}$ alkoxy, hydroxy, amino, halogen, aminoalkoxy, mono- or di-alkylaminoalkoxy, mono- or di-alkylaminoalkyl, phthaloylalkoxy, mono- or di-alkylaminoacylamino and acylamino; and $R_5$ is phenyl, thienyl, furyl, pyrryl and thiazolyl.

3. The method as claimed in claim 2, wherein for the compound of formula (I):

Ar is phenyl;

R is ethyl;

$R_1$ and $R_2$ are each hydrogen;

$R_3$ is hydrogen;

$R_4$ is hydroxy; and $R_5$ is phenyl.

4. A method for preparing (−)-(S)-N-(α-ethylbenzyl)-3-hydroxy-2-phenylquinoline-4-carboxamide comprising:

1) reacting 3-hydroxy-2-phenylquinoline-4-carboxylic acid, in a suitable solvent, with triethyl amine to form a first reaction mixture, cooling the first reaction mixture, and adding thionyl chloride to form a second reaction mixture comprising 6,14,22,30-Tetraphenyl-[1,5,9,13]tetraoxahexadecino[2,3-c:6,7-c':10,11-c":14,15-c'"]tetraquinoline-8,16,24,32-tetrone and Ethyl 3-acetoxy-2-phenylquinoline-4-carboxylate;

2) adding (S)-1-phenyl propylamine to the second reaction mixture to form a third reaction mixture comprising (−)-(S)-N-(α-ethylbenzyl)-3-hydroxy-2-phenylquinoline-4-carboxamide and (S)-2-Phenyl-4-[[(1-phenylpropyl)amino]carbonyl]-3-quinolinyl-3-hydroxy-2-phenyl-4-quinoline-carboxylate;

3) heating the third reaction mixture; and 4) optionally converting (−)-(S)-N-(α-ethylbenzyl)-3-hydroxy-2-phenylquinoline-4-carboxamide to a pharmaceutically acceptable salt.

5. A compound of formula (VII):

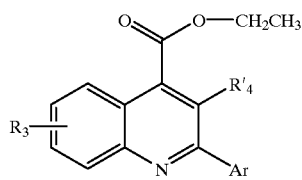

Ar is an optionally substituted phenyl group, or a naphthyl or $C_{5-7}$ cycloalkdienyl group, or an optionally substituted single or fused ring heterocyclic group, having aromatic character, containing from 5 to 12 ring atoms and comprising up to four hetero-atoms in the or each ring selected from S, O, N; and $R_3$ is hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —O(CH$_2$)$_r$—NT$_2$, in which r is 2, 3, or 4 and T is $C_{1-6}$ alkyl or it forms a heterocyclic group

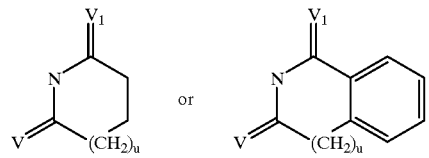

in which V and $V_1$ are hydrogen and u is 0, 1 or 2;

—O(CH$_2$)$_s$—OW$_2$ in which s is 2, 3, or 4 and W is $C_{1-6}$ alkyl; hydroxyalkyl, mono- or di-alkylaminoalkyl, acylamino, alkylsulphonylamino, aminoacylamino, mono- or di-alkylaminoacylamino; with up to four $R_3$ substituents being present in the quinoline nucleus; and $R'_4$ is OH or OAc.

6. The compound of formula (VII) according to claim 5, which is

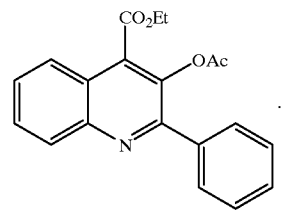

7. A compound of formula (VIII):

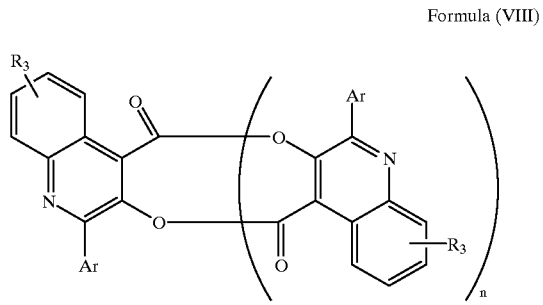

Formula (VIII)

wherein:

Ar and R₃ are as defined for a compound of formula (I) as claimed in claim 1; and n is 1 or 3.

8. The method as claimed in claim 1, wherein the compound of formula (I) is (−)-(S)-N-(α-ethylbenzyl)-3-hydroxy-2-phenylquinoline-4-carboxamide.

9. A method for preparing a compound of formula (Ia):

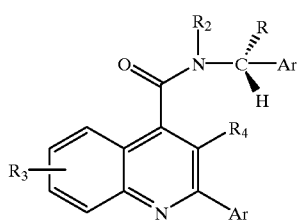

(Ia)

wherein:

Ar is an optionally substituted phenyl group, or a naphthyl or C₅₋₇ cycloalkdienyl group, or an optionally substituted single or fused ring heterocyclic group, having aromatic character, containing from 5 to 12 ring atoms and comprising up to four hetero-atoms in the or each ring selected from S, O, N;

R is linear or branched $C_{1-8}$ alkyl, $C_{3-7}$ cycloalkyl, $C_{4-7}$ cycloalkylalkyl, an optionally substituted phenyl group or a phenyl $C_{1-6}$ alkyl group, an optionally substituted five-membered heteroaromatic ring comprising up to four heteroatom selected from O and N, hydroxy $C_{1-6}$ alkyl, di $C_{1-6}$ alkylaminoalkyl, $C_{1-6}$ acylaminoalkyl, $C_{1-6}$ alkylcarbonyl, carboxy, $C_{1-6}$ alkoxycarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl; or is a group —(CH₂)$_p$— when cyclized onto Ar, where p is 2 or 3;

R₂ is hydrogen or $C_{1-6}$ linear or branched alkyl; and

R₃ and R₄, which may be the same or different, are independently hydrogen, $C_{1-6}$ linear or branched alkyl, $C_{1-6}$ alkenyl, aryl, $C_{1-6}$ alkoxy, hydroxy, halogen, nitro, cyano, carboxy, carboxamido, sulphonamido, trifluoromethyl, amino, mono- and di-$C_{1-6}$ alkylamino, —O(CH₂)$_r$—NT₂, in which r is 2, 3, or 4 and T is $C_{1-6}$ alkyl or it forms a heterocyclic group

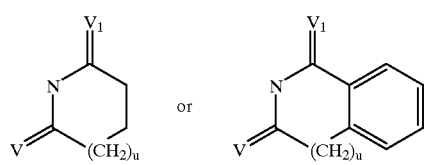

in which V and V₁ are hydrogen and u is 0, 1 or 2;

—O(CH₂)$_s$—OW₂ in which s is 2, 3, or 4 and W is $C_{1-6}$ alkyl; hydroxyalkyl, mono- or di-alkylaminoalkyl, acylamino, alkylsulphonylamino, aminoacylamino, mono- or di-alkylaminoacylamino; with up to four R₃ substituents being present in the quinoline nucleus; comprising:

1) adding a compound of formula (III):

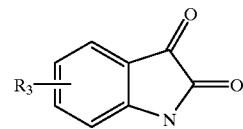

Formula (III)

to base in a suitable solvent, to form a first reaction mixture, adding to the first reaction mixture a compound of formula (IIa):

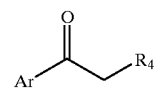

Formula (IIa)

to form a second reaction mixture, and heating the second reaction mixture to form a compound of formula (IVa):

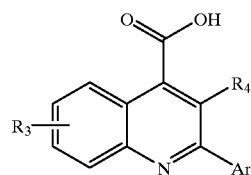

Formula (IVa)

2) isolating the compound of formula (IVa) and then reacting the compound of formula (IVa), in a suitable solvent, with a base to form a third reaction mixture, cooling the third reaction mixture, and adding a carbonyl-activating agent to form a fourth reaction mixture;

3) adding a compound of formula (Va):

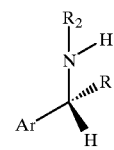

Formula (Va)

to the fourth reaction mixture to form a fifth reaction mixture;

4) heating the fifth reaction mixture; and 5) optionally converting the compound of formula (I) to a pharmaceutically acceptable salt thereof, wherein Ar, R, R₁, R₂, R₃, R₄, and R₅ as used in a compound of formulae (IIa), and (IVa) through (VIa) are as defined for a compound of formula (Ia).

10. A method for making a compound of formula (VII) as defined in claim 5, comprising:

1) adding a compound of formula (III):

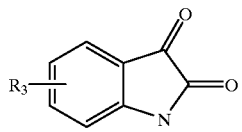

Formula (III)

to at least 2 to 6 equivalents of aqueous base in a suitable solvent to form a first reaction mixture, adding to the first reaction mixture a compound of formula (II'):

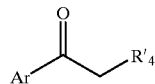

Formula (II')

to form a second reaction mixture, and heating the second reaction mixture to form a compound of formula (IV'):

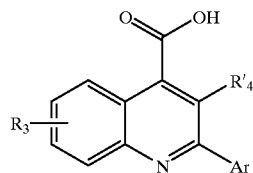

Formula (IV')

2) isolating the compound of formula (IV') and then reacting the compound of formula (IV'), in a suitable solvent with an amine base to form a third reaction mixture;

3) cooling the third reaction mixture below about 5° C. and adding a carbonyl-activating agent to form a fourth reaction mixture comprising a compound of formula (VII).

11. The method as claimed in claim 10, wherein in step 1 the aqueous base is selected from lithium hydroxide, sodium hydroxide, potassium hydroxide, calcium hydroxide or barium hydroxide.

12. The method as claimed in claim 11, wherein 4 equivalents of the aqueous base is used to form the first reaction mixture.

13. The method of claim 10, wherein in step 2 the amine base is selected from triethyl amine or diisopropylethyl amine.

14. The method of claim 10, further comprising adding an amine compound of formula (V) as defined in claim 1, to the fourth reaction mixture to form a fifth reaction mixture.

15. The method of claim 14, further comprising heating the fifth reaction mixture to obtain a compound of formula (I) as defined in claim 1.

16. The method of claim 15, further comprising converting the compound of formula (I) into a pharmaceutically acceptable salt.

17. The compound according to claim 7 which is selected from 6,14-diphenyl-[1,5]dioxocino[2,3-c:6,7-c'] diquinoline-8,16-dione or 6,14,22,30-Tetraphenyl-[1,5,9,13]tetraoxahexadecino[2,3-c:6,7-c':10,11-c":14,15-c'"] tetraquinoline-8,16,24,32-tetrone.

* * * * *